United States Patent [19]
Kenigsberg

[11] 4,168,703
[45] Sep. 25, 1979

[54] GASTROESOPHAGEAL REFLUX DIAGNOSTIC TOOL

[76] Inventor: Kenneth Kenigsberg, Vincent La., Syosset, N.Y. 11791

[21] Appl. No.: 816,546

[22] Filed: Jul. 18, 1977

[51] Int. Cl.$^2$ .............................................. A61B 5/10
[52] U.S. Cl. .................................... 128/748; 128/348; 73/700
[58] Field of Search .................. 128/2 R, 2 S, 2.05 D, 128/2.05 E, 4, 5, 8, 348, 349 R, 350 R; 73/700

[56] References Cited
U.S. PATENT DOCUMENTS

| | | | |
|---|---|---|---|
| 1,188,180 | 6/1916 | Kells | 128/350 R |
| 3,416,532 | 12/1968 | Grossman | 128/350 R |
| 3,437,088 | 4/1969 | Bielinski | 128/2 S |
| 3,480,003 | 11/1969 | Crites | 128/2 S |
| 3,771,527 | 11/1973 | Ruisi | 128/350 R |
| 4,030,481 | 6/1977 | Hill | 128/2 S |

FOREIGN PATENT DOCUMENTS

| | | | |
|---|---|---|---|
| 790091 | 11/1935 | France | 128/2 S |
| 176364 | 12/1965 | U.S.S.R. | 128/2 S |

*Primary Examiner*—Lee S. Cohen
*Attorney, Agent, or Firm*—Bauer & Amer

[57] ABSTRACT

A tool for diagnosing a gastroesophageal reflux condition whereby the pressure at selected locations along the gastroesophageal tract in a body may be measured without disturbing the relative position of the device after the same is positioned in the body each time a new location of the tract is selected for measuring the internal pressure thereat in which the tool comprises a flexible, hollow sleeve and a tubular member arranged for sliding longitudinal movement therein with an opening in the tubular member cooperating with a selected one of a plurality of spaced apertures on the sleeve to provide a pressure measurement at the selected aperture. Fixed tubes are additionally provided on the sleeve for monitoring the pressure at predetermined locations in the body.

11 Claims, 4 Drawing Figures

U.S. Patent     Sep. 25, 1979     4,168,703
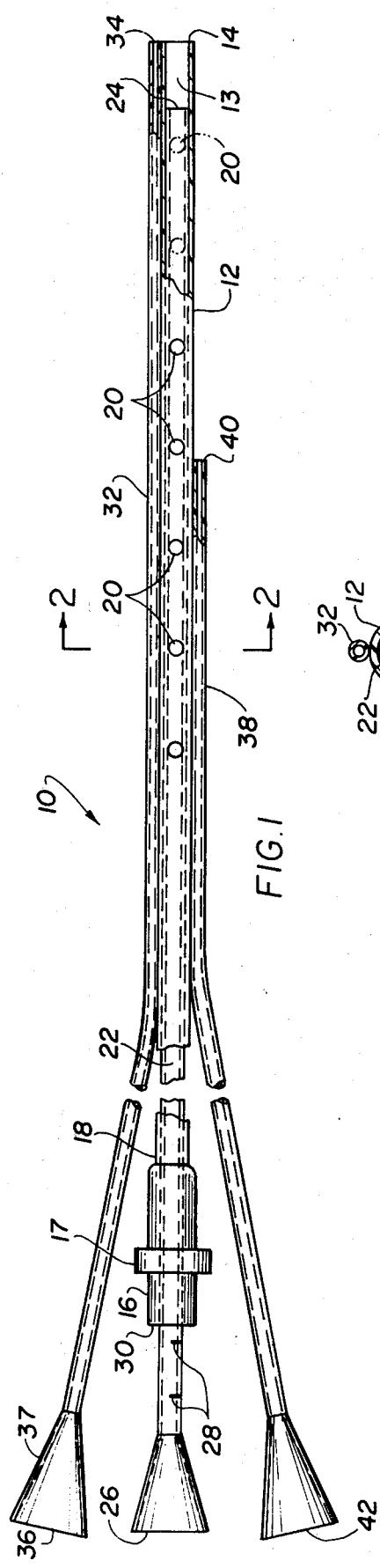
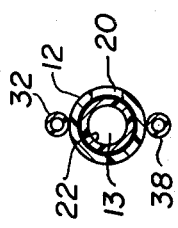
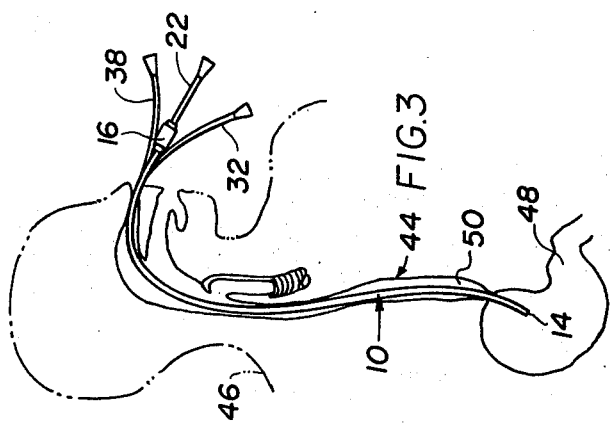
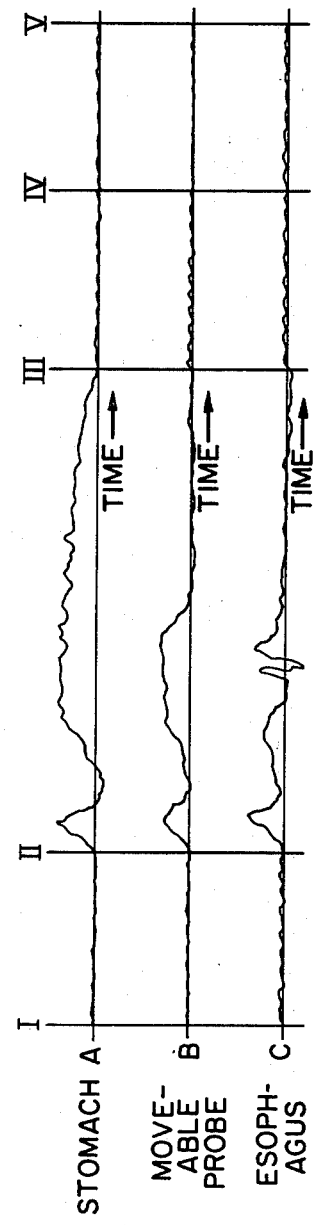

GASTROESOPHAGEAL REFLUX DIAGNOSTIC TOOL

BACKGROUND OF THE INVENTION

This invention relates to diagnostic devices used to test the operation of the various functional systems of the human body and, more particularly, to a gastroesophageal reflux diagnostic tool.

Gastroesophageal reflux is a medical condition that is particularly significant in infants. The retrograde surging of gastric content after a child has eaten can cause many problems including, but not limited to, failure to thrive, aspiration pneumonia and inflammation of the esophagus.

It has been found that the problem in those with significant gastroesophageal reflux is often in the lower esophagus, just above the junction with the stomach. This area, known as the sphincter, normally has a continually high pressure than either the stomach below or esophagus above. This higher pressure prevents the backward flow of gastric content at most times. In effected individuals, this area of high pressure in the lower esophagus is absent or has a much diminished pressure as compared to that of normal individuals. The decrease or absence of pressure in the lower esophagus allows the food to flow back, resulting in the pathologic changes described above.

A commonly used method of confirming the diagnosis of gastroesophageal reflux is to measure the pressure in the lower esophagus and stomach, as well as the pressure at several points therebetween. Absence of a high pressure area between the esophagus and the stomach is strong evidence of gastroesophageal reflux.

The usual method of measuring these pressures is to insert a cluster of several tubes through the nose or mouth into the stomach. A device for this purpose is taught in U.S. Pat. No. 3,437,088 to Bielinski in which each of the tubes has an opening set or relatively fixed at different levels so that pressures can be obtained only at such various heights within the stomach and esophagus. To determine the presence or absence of a high pressure area in the lower esophagus, the entire cluster of tubes is withdrawn from the stomach while continuous pressure readings are taken. This measurement technique works reasonably well in cooperative older children and adults. However, in infants, the movement of the tube to determine the pressure irritates the child, causing him to move, cry or cough. The movement of the diaphragm and contraction of the abdominal wall musculature causes an increase of the pressure within the stomach and esophagus far exceeding the normal pressures which are being observed. Such continual crying and moving of the infant prevents the accurate measurement of internal pressures along the gastroesophageal tract and squanders much valuable time waiting for the child to settle which could be more effectively utilized by the doctor.

It is, therefore, an object of the present invention to provide a gastroesophageal reflux diagnostic tool with which measurements of pressure at selected locations between the stomach and the lower esophagus may be obtained without disturbing the position of the tool in the gastroesophageal tract of the patient each time a new measurement is to be taken.

It is a further object of the present invention to provide such a diagnostic tool including means for continually observing the pressure in the stomach and in the lower esophagus while measurements at selected locations therebetween are taken without disturbing the patient.

Further objects and features of the invention reside in the provision and use of an easy to use structure to accomplish the aforementioned objects.

The above description, as well as further objects, features and advantages of the present invention, will be more fully appreciated by reference to the following detailed description of a presently preferred, but nonetheless illustrative, embodiment in accordance with the present invention, when taken in conjunction with the accompanying drawings. It is to be understood, however, that the drawings are designed for the purpose of illustration only and not as a definition of the limits of the invention for which reference should be made to the appending claims.

DESCRIPTION OF THE DRAWINGS

In the drawings, wherein similar reference characters denote similar elements throughout the several views:

FIG. 1 is a side elevational view partially broken away of a gastroesophageal reflux diagnostic tool constructed according to the teaching of the present invention;

FIG. 2 is an elevational view along the length of the gastroesophageal reflux diagnostic tool of the present invention taken along the lines 2—2 in FIG. 1;

FIG. 3 is a view of a diagnostic tool of the present invention operationally positioned in the gastroesophageal tract of a human body; and FIG. 4 is a chart depicting pressures in the gastroesophageal tract of a body as measured using the diagnostic tool of the present invention positioned in the manner shown in FIG. 3.

DETAILED DESCRIPTION OF THE PREFERRED EMBODIMENT

Referring now to the drawing, there is shown in FIGS. 1 and 2 a gastroesophageal reflux diagnostic tool, generally identified by the numeral 10, for insertion into an internal cavity of a human body, in which the tool 10 is constructed in accordance with the present invention. The tool 10, and more specifically the various parts thereof as will be detailed and described hereafter, is constructed of a flexible material such as a plastic or the like and may be advantageously transparent to permit its internal inspection after cleansing and sterilization of the same. Since the proper cooperation of the various components of the tool 10 is necessary for its successful use, transparency offers the further advantage of insuring efficient operation of the tool 10 prior to insertion of the same into an internal body cavity in a manner to be described.

The tool 10 includes as a component thereof an outer sheath 12 which is constructed as an elongated tubular member. The sheath 12 has a hollow interior 13 substantially throughout its length and terminates in a distal end 14 which is preferably open and in a hollow manipulating body 16 at its proximal end 18. The manipulating body 16 may be of any convenient shape and may be provided with a raised surface portion 17 to facilitate the grasping and handling thereof in a manner to be described.

A plurality of relatively spaced openings 20 is provided along at least a portion of the length of the sheath 12 for communication with the hollow interior 13 thereof. The openings 20 are preferably substantially equally spaced from each other beginning adjacent the distal end 14 of the sheath 12. Although the openings 20 need not be provided along the entire length of the sheath 12, they should be provided over at least a substantial portion thereof to permit pressure measurements over a wide range of locations as described hereinafter. A distance of approximately 2 cm between adjacent openings 20 has been found to provide a satisfactory range of results in utilizing the tool 10 in a manner to be described. However, this dimension should not constitute a limitation on the scope of the invention. It should be further understood that although the openings 20 are depicted in FIG. 1 as being of circular cross-section, the actual configuration thereof is a matter of design choice and it is not intended that their shape be so limited.

A movable probe 22 is formed as a hollow tube and sized for relative longitudinal frictionless sliding movement within the interior 13 of the sheath 12. The probe 22 terminates in an end 24 for movement within the sheath 12. The end 24 is preferably open, although an opening could alternatively be provided adjacent thereto. The opposite end 26 of the probe 22 is adapted for connection to a pressure sensitive means and thus may, by way of example only, be outwardly tapered as illustrated in FIG. 1.

As this description proceeds, it will become apparent that it would be advantageous if the open end 24 of the probe 22 were constrained against rightward movement in FIG. 1 beyond the open distal end 14 of the sleeve 12. Toward this end, the length of the movable probe 22 may be conveniently sized such that the rightward insertion of the same into the sleeve 12 will be halted through a contact of a portion of the tapered end 26 with the manipulating body 16 at a point at which the probe end 24 reaches the sleeve distal end 14. This will thereby insure that the open end 24 of the probe 22 will be slidable only within the hollow interior of the sleeve 12 and not beyond its distal end 14.

A multiplicity of relatively spaced indicies 28 may be provided along the length of the movable probe 22. The indicies 28 should be substantially equally spaced from one another and, as will become clear, the distance between adjacent indicies 28 should be equal to the distance between adjacent ones of the openings 20 on the sheath 12. As will also become apparent, alignment of a selected one of the indicies 28 with the rearward edge 30 of the manipulating body 16 will serve to locate the movable probe 22 in a selected position relative to the outer sheath 12. Although the indicies 28 are depicted in FIG. 1 as a series of lines or marks, it should be obvious that other indicating means, such as numbers or similar figures, may be provided to more precisely indicate the position of the probe 22 relative to the sheath 12.

A first reference member 32 is fixed for a portion of its length on the outer sheath 12. Member 32 is configured as an elongated, hollow tube and may be formed integral with the sheath 12 or permanently affixed thereto. Although shown positioned on the surface of the sheath 12 in the drawing, the member 32 may be located within a suitably modified sheath (not shown) provided its placement within the sheath does not interfere with the free movement of the probe 22 therein.

The member 32 terminates in an end 34 adjacent the distal end 14 of the sheath 12. The end 34 is preferably open, although an opening could alternatively be provided in the member 32 substantially adjacent the end 34. The opposite end 36 of the member 32 extends flexibly away from the sheath 12 and is provided with means for attachment to a pressure sensitive means, as for example the outwardly tapered portion 37 illustrated in FIG. 1.

A second reference member 38 is similarly provided on the sheath 12 and fixed thereto for a portion of its length in the form of an elongated, hollow tube. The member 38 may be carried on the surface of the sheath 12, as shown, or internally thereof, as described above in relation to first member 32. As depicted in FIG. 1, the member 38 terminates in an open end 40 at a fixed position intermediate the proximal and distal ends 18 and 14 of the sheath 12. As the description proceeds, however, it will become apparent that the end 40 need not be open if instead an opening is provided in the second member 38 at a position intermediate the proximal and distal ends of the sheath 12. The opposite end 42 of the second member 38 may be outwardly tapered for attachment to a pressure sensitive means.

In use, and as seen in FIG. 3, the tool 10 is operatively positioned in the gastroesophageal tract generally identified as 44 of a patient 46. To facilitate its insertion into the body, the tool 10 may first be lightly lubricated with a suitable lubricant or water. With the probe 22 fully inserted into the sheath 12, tool 10 is then introduced into the body through the nose or mouth of the patient 46 to position the distal end 14 of the sheath 12, and with it the adjacent open end 34 of first member 32, in the stomach 48. Properly positioned, this will also serve to locate the fixed open end 40 of second member 38 in the lower esophagus 50. It has been found that a distance of approximately 10 cm between the ends 34 and 40 of the members 32 and 38 respectively will position end 40 of member 38 in the lower esophagus of a child when the tool 10 is positioned as shown in FIG. 3.

After insertion of the tool 10 into the body, water is infused through the probe 22 and the reference members 32 and 38 at their respective connections 26, 36 and 42. This infusion is continued throughout the period of diagnostic use of the tool 10. An infusion rate in each of 0.764 ml of water per minute yields good results without introducing an excessive quantity of liquid into the body during the use of the diagnostic tool 10. An extremely sensitive strain gauge is attached to the ends 26, 36 and 42 of probe 22 and members 32 and 38 respectively to measure the resistance to the outflow of the infused water from the tool 10 and into the gastroesophageal track 44. A chart recorder may be employed to make a permanent record of the test results.

It should be clear, therefore, that first reference member 32 will provide a measurement of the pressure at its open end 34 positioned in the stomach 48. Likewise, second reference member 38 will provide an indication of the pressure at its open end 40 positioned in the lower esophagus 50. By sliding the movable probe 22 relative to the stationary outer sheath 12 to align the probe's open end 24 with selected ones of the sheath openings 20, pressure measurements may be obtained at incremental locations along the elongation of the sheath 12, and particularly at such locations between the stationary ends of the members 32 and 38, corresponding to the positions of the openings 20. Selected ones of the indicies 28 may be aligned with the rearward edge 30 of the manipulating body 16 to coincide the position of the probe end 24 with selected sheath openings 20. Thus, while constantly monitoring the pressure in the stomach 48 and in the lower esophagus 50, pressure measurements may be obtained therebetween at selected incremental locations by varying the position of the probe 22 within the outer sheath 12.

The chart of FIG. 4 illustrates the advantages inherent in the use of the tool 10 of the present invention over the teachings of the prior art. Line A represents the pressure in the stomach as measured at the open end 34 of first reference member 32. Line B is the pressure as measured at the end 24 of movable probe 22. Line C shows the lower esophageal pressure measured by the second reference member 38 at its open end 40.

Point I illustrates the probe 22 as being fully inserted into the sheath 12 to position the probe end 24 in the stomach with the tool 10 positioned as shown in FIG. 3. The readings between points I and II thus constitute the reference measurements in the stomach at line A and in the lower esophagus at line C. It should be noted that with the probe 22 fully inserted into the sheath 12 to position the probe end 24 adjacent the open distal end 14 of the sheath 12, the reading at line B mirrors that of line A, the stomach reference measurement, because the end of the probe 22 is in the stomach at that moment.

The readings between points II and III simulate one of the problems inherent in the prior art devices, such as that taught by Bielinski, U.S. Pat. No. 3,437,088, in which the entire device must be moved to vary the location in the gastroesophageal tract 44 at which readings are to be taken. Movement of the entire device in the tract 44 disturbs and irritates the child, causing him to move, cry and/or cough. The resultant increase in pressure within the stomach and esophagus far exceeds the normal pressures which are being observed, as is easily seen between points II and III in FIG. 4. A significant amount of time is then required to calm and settle the child before any further meaningful readings can be taken.

At point III the probe 22 has been moved relative to the sheath 12 to position the probe end 24 adjacent a selected sheath opening 20 positioned in the lower esophagus. It is clear from an examination of FIG. 4 between points III and IV that line B simulates or approximates the waveform seen on line C, the lower esophageal reference measurement, because at that moment the probe end 24 is in the esophagus with the tube end 40 at which the reference reading C is taken. At point IV, the probe 22 has been returned to its fully inserted position in the sheath 12 and its waveform at line B is again seen to have assumed the shape of the stomach reference measurement similar to that at line A.

Thus, it will be observed that movement of the probe 22 within and relative to the sheath 12 is accomplished without disturbing the position of the sheath 12 in the gastroesophageal tract 44 of the patient 46. Pressure readings at various selected positions between the stomach 48 and the lower esophagus 50 may therefore be taken without disturbing the patient or causing his discomfort, and with the certainty that the readings obtained will be accurate and uninfluenced by externally induced factors.

While there have been shown and described and pointed out the fundamental novel features of the invention as applied to a preferred embodiment thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. In an elongated reflux diagnostic tool having a flexible member for the infusion of liquid therethrough into a body at different spaced points along the elongation of said tool and with openings defined therein for the purpose of providing standard reference pressure readings thereat, the invention comprising:

said flexible member having a hollow interior, apertures spaced along the length of said flexible member extending from the interior to the exterior thereof, and a flexible tubular element having a hollow interior of elongated length and an opening slidably movable relative to and lengthwise of said flexible member within the interior thereof selectively between certain of said apertures for the infusion of liquid through said flexible element and through said selected aperture to obtain a pressure measurement of the body at said selected aperture, said tubular element being slidable within said flexible member without disturbing the relative location and position of said flexible member within the body during the liquid infusion of the body at said selected aperture and the obtaining of a reading of the pressure in the body at said selected aperture and extending outward from the proximal end of said flexible member and including means to align said opening of said tubular element with a selected aperture.

2. In the tool of claim 1, said apertures being substantially equally spaced from adjacent ones of the apertures.

3. In the tool of claim 1, the invention further comprising means on said tubular element for indicating the position of said tubular element relative to said flexible member and for aligning said tubular element with said selected aperture to obtain a pressure measurement of the body at said selected aperture.

4. A perfusion catheter for insertion into an internal portion of a human body and for taking pressure measurements therein, said perfusion catheter comprising:

a flexible outer sheath having a proximal and a distal end and a plurality of relatively spaced apertures along at least a portion of the length of said sheath, a first flexible tubular member on said sheath and integral therewith for the infusion of liquid therethrough and having an opening adjacent the distal end of said sheath and an end for attachment to a pressure responsive means to provide a pressure reading at said opening as a first reference standard, a second flexible tubular member on said sheath and integral therewith for the infusion of liquid therethrough and having an opening fixed intermediate said proximal and distal ends of said sheath, and an end for attachment to a pressure responsive means to provide a pressure reading at said opening of said second member as a second reference standard, and a third flexible tubular member for the infusion of liquid therethrough and movable longitudinally and slidable within and relative to said outer sheath and having an opening disposed for sliding movement within said sheath and an end adapted for attachment to a pressure responsive means to provide a pressure reading at said opening of said third member when the same is at a selected position along the length of said sheath corresponding to the location of a selected one of said plural relatively spaced apertures on said sheath.

5. A perfusion catheter as in claim 4, the distal end of said sheath being open to permit the outflow therefrom of liquid infused through said third tubular member within said sheath.

6. A perfusion catheter as in claim 4, wherein:
said opening in said first member is at the end thereof opposite said end for attachment to a pressure responsive means,
said opening in said second member is at the end thereof opposite said end for attachment to a pressure responsive means, and
said opening in said third member is at the end thereof opposite said end for attachment to a pressure responsive means.

7. A perfusion catheter as in claim 4, including means on said third tubular member for indicating the position of said third member relative to said sheath to permit a user of the catheter to coincide the position of the opening of said third member with a selected one of said plural relatively spaced apertures on said sheath to measure the pressure at the location of said selected aperture.

8. A perfusion catheter as in claim 7, said indicating means being a plurality of relatively spaced markings along at least a portion of the length of said third member, the distance between adjacent ones of said plural markings being equal to the distance between adjacent ones of said plural apertures on said sheath.

9. A perfusion catheter as in claim 4, including means on the proximal end of said sheath for manipulation of the same and for receiving through said manipulating means said third tubular member for relative sliding movement therethrough and into said sheath without disturbance of said sheath or a body into which the same is inserted to facilitate the insertion into and removal from an internal portion of a human body said outer sheath.

10. A gastroesophageal reflux diagnostic tool for insertion into a patient's gastroesophageal tract for measuring the pressure between the esophagus and the stomach using a perfused catheter technique, said tool comprising:
a flexible, hollow outer sheath having a proximal and a distal end and a plurality of relatively spaced openings along at least a portion of the length of said sheath, said proximal and distal ends being open, said distal end being adapted to be positioned in the patient's stomach,
a first flexible tubular member on said sheath and formed integral therewith to provide a stomach pressure reference measurement, said first tubular member terminating in an open end adjacent the open distal end of said sheath, the other end of said first member having means for connection to a pressure responsive indicating means for the purpose of taking a pressure measurement at said open end of said first member,
a second flexible tubular member on said sheath and formed integral therewith to provide an esophageal pressure reference measurement, said second tubular member terminating in an open end fixed intermediate the proximal and distal ends of said sheath, the other end of said second member having means for connection to a pressure responsive indicating means for the purpose of taking a pressure measurement at said open end of said second member,
a third flexible tubular member adapted for longitudinal movement within and relative to said sheath and having an open end disposed for longitudinal movement within said sheath and an opposite end having means for connection to a pressure responsive indicating means, and a plurality of relatively spaced indicia on at least a portion of said third tubular member for indicating the position of the open end of said third member relative to the open distal end of said sheath, the distance between adjacent ones of said plural indicia being equal to the distance between adjacent ones of said plural openings on said sheath, and
a manipulating body on the proximal end of said sheath for manipulation of the sheath and for its insertion into and removal from the gastroesophageal tract of the patient, and for receiving through the manipulating body said third tubular member, whereby the pressure at a selected location along the gastroesophageal tract may be measured by moving said third tubular member within and relative to said stationary outer sheath to position the open end of said third member adjacent a selected one of the plural relatively spaced openings on said sheath without disturbance of the position of said stationary outer sheath in the patient's gastroesophageal tract.

11. A diagnostic tool as in claim 10, wherein said first and second tubular members are positioned on the surface of said sheath.

* * * * *